US012211125B2

(12) United States Patent
Frushour

(10) Patent No.: US 12,211,125 B2
(45) Date of Patent: Jan. 28, 2025

(54) SYSTEMS AND METHODS FOR RADIOGRAPHIC EVALUATION OF A NODULE FOR MALIGNANT SENSITIVITY

(71) Applicant: Covidien LP, Mansfield, MA (US)

(72) Inventor: Scott E. M. Frushour, Boulder, CO (US)

(73) Assignee: Covidien LP, Mansfield, MA (US)

(*) Notice: Subject to any disclaimer, the term of this patent is extended or adjusted under 35 U.S.C. 154(b) by 385 days.

(21) Appl. No.: 17/559,919

(22) Filed: Dec. 22, 2021

(65) Prior Publication Data
US 2023/0196639 A1  Jun. 22, 2023

(51) Int. Cl.
*G06T 11/00* (2006.01)
*A61B 34/00* (2016.01)
(Continued)

(52) U.S. Cl.
CPC ............ *G06T 11/008* (2013.01); *A61B 34/10* (2016.02); *A61B 34/20* (2016.02); *A61B 34/25* (2016.02);
(Continued)

(58) Field of Classification Search
CPC .................. G06T 11/008; G06T 15/08; G06T 2207/10081; G06T 2207/10088; G06T 2207/30064; G06T 11/00; G06T 7/0012; G06T 7/62; G06T 15/00; G06T 2200/04; G06T 2207/10064; G06T 2207/10104; G06T 2207/10116; G06T 2207/10136; G06T 2207/30016; G06T 2207/30056; G06T 2207/30084; G06T 2207/30096; G06T 2210/41; A61B 34/10; A61B 34/20; A61B 34/25; A61B 2034/107; A61B 5/4842; G06V 10/82; G06V 40/67
See application file for complete search history.

(56) References Cited

U.S. PATENT DOCUMENTS

| 10,290,101 B1 | 5/2019 | Podilchuk et al. |
| 11,010,610 B2 | 5/2021 | Stumpe |

(Continued)

OTHER PUBLICATIONS

Extended European Search Report issued in European Patent Application No. 22215326.4 dated May 25, 2023.

(Continued)

*Primary Examiner* — Dung D Tran
(74) *Attorney, Agent, or Firm* — Weber Rosselli & Cannon LLP

(57) ABSTRACT

Systems and methods of guiding a clinician in a medical procedure for a nodule involve receiving three-dimensional (3D) image data, generating a volumetric vector map based on the 3D image data, and displaying the volumetric vector map in a way, e.g., via a heat map, that assists a clinician in performing a medical procedure. The systems and methods involve identifying volumetric parameters of the nodule in the 3D image data, generating a voxel map based on the volumetric parameters, identifying a maximum attenuation value in the 3D space of the voxel map, applying a differential equation, e.g., a gradient, to the 3D space of the voxel map from a voxel with the maximum attenuation value to other voxels within the voxel map, and generating a volumetric vector map based on the result of applying the differential equation.

20 Claims, 5 Drawing Sheets

(51) Int. Cl.
*A61B 34/10* (2016.01)
*A61B 34/20* (2016.01)
*G06T 15/08* (2011.01)
*G06V 10/82* (2022.01)
*G06V 40/60* (2022.01)

(52) U.S. Cl.
CPC .............. *G06T 15/08* (2013.01); *G06V 10/82* (2022.01); *G06V 40/67* (2022.01); *A61B 2034/107* (2016.02)

(56) References Cited

U.S. PATENT DOCUMENTS

| | | | | |
|---|---|---|---|---|
| 11,321,842 | B1* | 5/2022 | Tiwari | G06T 7/0014 |
| 11,701,066 | B2* | 7/2023 | Yan | G06F 18/21 |
| | | | | 382/131 |
| 2002/0006216 | A1* | 1/2002 | Armato, III | G06T 7/174 |
| | | | | 382/172 |
| 2002/0141627 | A1* | 10/2002 | Romsdahl | A61B 6/032 |
| | | | | 382/154 |
| 2003/0223627 | A1* | 12/2003 | Yoshida | G06T 7/155 |
| | | | | 382/128 |
| 2013/0012805 | A1 | 1/2013 | Penn | |
| 2018/0247195 | A1 | 8/2018 | Kumar et al. | |
| 2020/0085382 | A1 | 3/2020 | Taerum et al. | |

OTHER PUBLICATIONS

Ming Yang et al: "False Positive Reduction in Lung GGO Nodule Detection with 3D Volume. Shape Descriptor", 2007 IEEE International Conference on Acoustics, Speech and Signal Processing, IEEE, Piscataway, NJ, USA, Apr. 15, 2007 (Apr. 15, 2007), pp. 1-437, XP031462892.

Nappi J et al: "Automated Detection of Polyps with CT Colonography", Academic Radiology, Elsevier, Amsterdam, NL, vol. 9, No. 4, Apr. 1, 2002 (Apr. 1, 2002), pp. 386-397, XP027131079.

Wiemker R et al: "Filter learning and evaluation of the Computer Aided Visualization and Analysis (CAVA) paradigm for pulmonary nodules using the LIDC-IDRI database", Proceedings of SPIE, IEEE, US, vol. 7624, Jan. 1, 2010 (Jan. 1, 2010), pp. 76272U-1, XP002674998.

Nitadori et al., "Preoperative Consolidation-to-Tumor Ratio and SUVmax Stratify the Risk of Recurrence in Patients Undergoing Limited Resection for Lung Adenocarcinoma ≤2 cm", Ann Surg Oncol. Dec. 2013 ; 20(13): 4282-4288.

Takahashi et al., "Tumor invasiveness as defined by the newly proposed IASLC/ATS/ERS classification has prognostic significance for pathologic stage IA lung adenocarcinoma and can be predicted by radiologic parameters", The Journal of Thoracic and Cardiovascular Surgery, Jan. 2014 pp. 54-59.

Woo Sik Yu et al., "Three-Dimensional Ground Glass Opacity Ratio in CT Images Can Predict Tumor Invasiveness of Stage IA Lung Cancer", Yonsei Med J Sep. 2016;57(5):1131-1138.

Wu HR, Liu CQ, Xu MQ, et al. A Retrospective Study of Mean Computed Tomography Value to Predict the Tumor Invasiveness in AAH and Clinical Stage la Lung Cancer. Zhongguo Fei Ai Za Zhi, 2018, 21(3): 190-196.

* cited by examiner

SYSTEMS AND METHODS FOR RADIOGRAPHIC EVALUATION OF A NODULE FOR MALIGNANT SENSITIVITY

FIELD

This disclosure relates to systems and methods for radiographically evaluating a nodule for malignant sensitivity and guiding a clinician in a medical procedure based on the results of the evaluation. In particular, this disclosure is directed at improved systems and methods of generating a volumetric vector map based on 3D image data and displaying the volumetric vector map in a way that assists the clinician in a medical procedure.

BACKGROUND

Lung cancer appears in the form of nodules or lesions that are attached to the lung wall, major vessels, or other linear structures, or appears as solitary nodules within the lung. Lung cancer tends to be heterogenous in nature, resulting in a need to biopsy across a broad range of the nodule to confidently assess for the presence of disease. As the nodule is volumetric in nature, determining the presence of disease in the nodule may require multiple passes and targets within a nodule to make an accurate determination.

Prior to insulting a patient's tissue, a CT scan may be acquired and read by a radiologist for various parameters that can be used to assess the nature of the lung cancer nodule. A radiologist may assess the maximum cross-sectional length in two planes, which may be used to determine the size of the lung cancer nodule. However, because of the heterogenous nature of lung cancer nodules, such an assessment may not lead to an accurate characterization of the lung cancer nodule.

SUMMARY

In one aspect, the disclosure features a system including a processor, a display coupled to the processor, and a memory coupled to the processor. The memory has stored thereon instructions, which when executed by the processor, causes the processor to: receive a three-dimensional (3D) image data set of a nodule, identify volumetric parameters of the nodule in the 3D image data set, generate a 3D voxel map based on the volumetric parameters of the nodule, determine maximum and minimum attenuation values in the 3D voxel map, calculate a gradient of the voxel map based on the maximum and minimum attenuation values, generate a volumetric vector map based on a result of calculating the gradient and the maximum and minimum gradient values across the voxel map, and cause the display to display the volumetric vector map.

Implementations of the system may include one or more of the following features. The memory may have stored thereon instructions, which when executed by the processor, cause the processor to generate vector arrows based on the volumetric vector map and cause display of the vector arrows on the display. The memory may have stored thereon instructions, which when executed by the processor, cause the processor to generate a heat map based the volumetric vector map and cause display of the heat map on the display. The memory may have stored thereon instructions, which when executed by the processor, cause the processor to overlay the volumetric vector map on the 3D image data set and cause display of the volumetric vector map overlaid on the 3D image data set on the display. The 3D image data set may be a computed tomography (CT) image data set, a magnetic resonance imaging (MRI) data set, a fluoroscopic image data set, an X-Ray image data set, an ultrasound image data set, or a positron emission tomography (PET) image data set. The memory may have stored thereon instructions, which when executed by the processor, cause the processor to apply a differential equation across a 3D space of the voxel map to generate the volumetric vector map.

In another aspect, the disclosure features a method. The method includes acquiring three-dimensional (3D) image data of a nodule, identifying a volumetric boundary of the nodule in the 3D image data, generating a voxel map based on the volumetric boundary of the nodule, identifying a maximum Hounsfield unit in a 3D space of the voxel map, applying a differential equation across the 3D space of the voxel map from a voxel with the maximum Hounsfield unit to a margin boundary, and generating a volumetric vector map based on a result of applying the differential equation across the 3D space of the voxel map.

Implementations of the method may include one or more of the following features. The nodule may be a tumor of a lung, a liver, a kidney, a pancreas, or a brain. Applying a differential equation across the 3D space of the voxel map may include applying a gradient function. The 3D image data may be computed tomography (CT) data, a magnetic resonance imaging (MRI) data, fluoroscopic image data, X-Ray image data, ultrasound image data, or positron emission tomography (PET) image data.

The method may include generating a 3D matrix of vector arrows based on the volumetric vector map and displaying the 3D matrix of vector arrows. The method may include generating a heat map based on the volumetric vector map and displaying the heat map. The method may include displaying the 3D image data and overlaying the volumetric vector map on the 3D image data. The method may include identifying the volumetric boundaries of the nodule using a convolutional neural network. In another aspect, the disclosure features another system including a processor and a memory coupled to the processor. The memory may have stored thereon instructions, which when executed by the processor, causes the processor to: receive three-dimensional (3D) image data of a nodule, identify volumetric boundaries of the nodule in the 3D image data, generate a voxel map based on the volumetric boundaries of the nodule, determine maximum and minimum Hounsfield units in a 3D space of the voxel map, calculate a gradient from a voxel with the maximum Hounsfield unit to a voxel with the minimum Hounsfield unit, generate a volumetric vector map based on a result of calculating the gradient, and cause display of the volumetric vector map.

Implementations of the method may include one or more of the following features. The 3D image data may be computed tomography (CT) image data, a magnetic resonance imaging (MRI) data, fluoroscopic image data, X-Ray image data, ultrasound image data, or positron emission tomography (PET) image data. The memory may have stored thereon instructions, which when executed by the processor, cause the processor to display the 3D image data and overlay the volumetric vector map on the 3D image data. The memory may have stored thereon instructions, which when executed by the processor, cause the processor to display a guide for a medical procedure in a user interface based on the volumetric vector map. The medical procedure may include placing an ablation tool, depositing pharmaceuticals, placing a biopsy tool, or cutting tissue. The memory may have stored thereon instructions, which when executed by the processor, cause the processor to generate a heat map based on the volumetric vector map and display the heat map.

BRIEF DESCRIPTION OF THE DRAWINGS

Various examples of embodiments are illustrated in the accompanying figures. It will be appreciated that for simplicity and clarity of the illustration, elements shown in the figures referenced below are not necessarily drawn to scale. Also, where considered appropriate, reference numerals may be repeated among the figures to indicate like, corresponding or analogous elements. The figures are listed below.

DETAILED DESCRIPTION

In diagnosing lung cancer tumors, clinicians often direct a biopsy needle at the center of the tumor with the hope that the biopsy sample will lead to an accurate diagnosis of the tumor. If the biopsy sample looks suspicious of lung cancer but is not malignant, the clinician obtains additional biopsy samples around the lateral boundaries of the tumor until the clinician exhausts the clinician's options or the clinician confirms that the tumor is malignant. However, such a process is tedious and time consuming.

Figure 3:
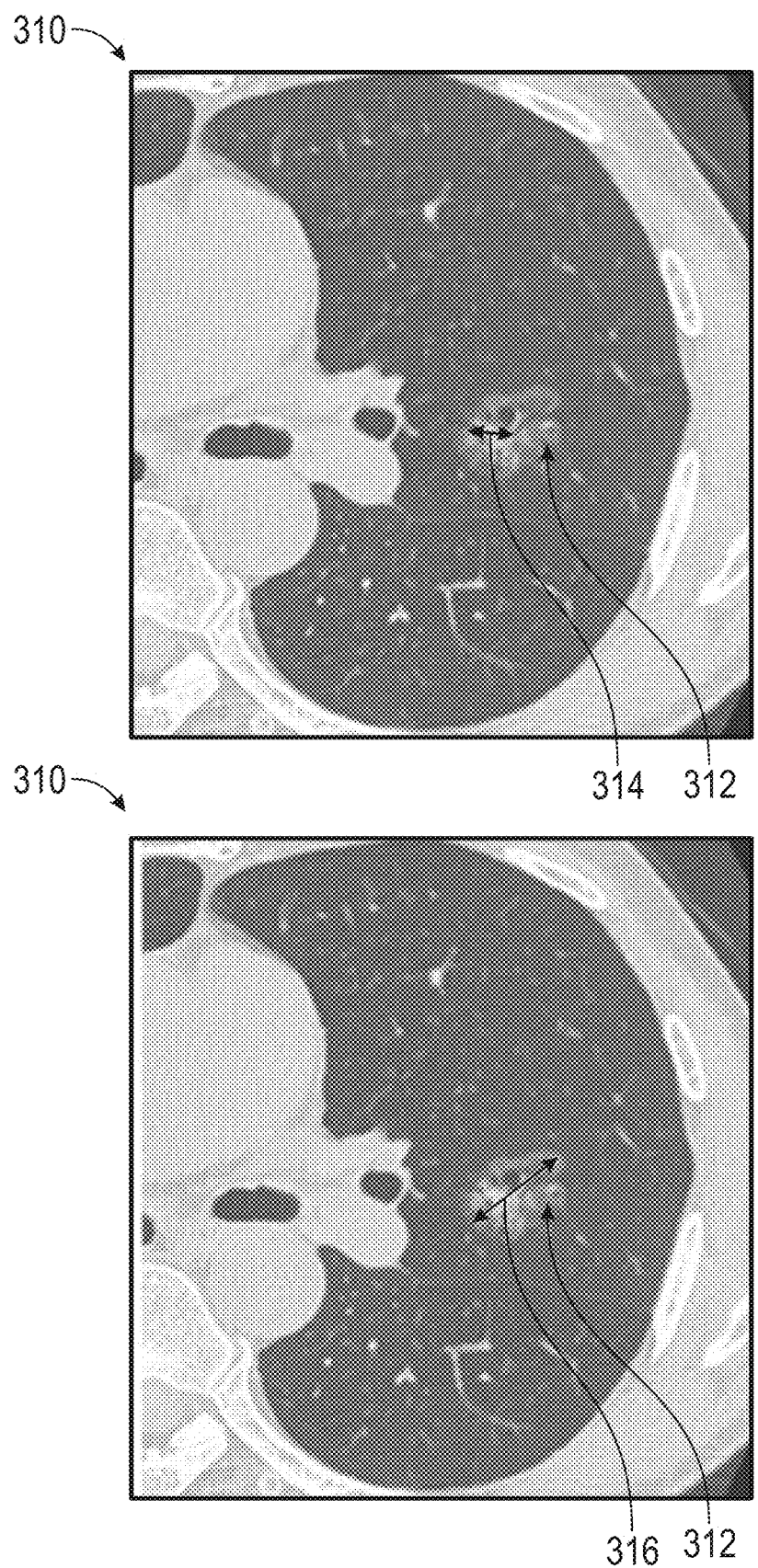
FIG. 3 is a schematic diagram that illustrates an example of a consolidation/tumor (C/T) ratio measurement.

A measurement called the consolidation/tumor (C/T) ratio or consolidation ratio may be used to accurately determine the invasiveness of a tumor. As illustrated in FIG. 3, this measurement is performed on a 2D planar CT slice 310 by measuring the maximum diameter of consolidation 314 and dividing the maximum diameter of consolidation by the maximum diameter 316 of the tumor 312. The C/T ratio has been correlated with more aggressive and invasive lung cancers, which have lower survival rates and higher recurrence rates. For example, ground-glass opacities may be associated with benign inflammations or low-grade cancerous mutations, and may have low C/T ratios.

Research suggests the measurement should be performed volumetrically by including a third plane in the measurement. Hence, in aspects, the systems and methods of this disclosure identify the highest point of consolidation in 3D image data and calculate the gradient of all vectors towards normalized tissues or Hounsfield values outside the margin boundary of a nodule. The vector or range of vectors with the steepest gradient may suggest where the most aggressive or active component of the tumor resides. Similarly, in resection, there may rest a plane tangent to this gradient where the clinician may want to take the largest lateral margin from the organ. Displaying this gradient in an appropriate form to the clinician may assist the clinician in determining where the clinician should have the most interest from a biopsy and therapy delivery perspective.

This micro-level guidance to the clinician on where to focus the clinician's efforts may provide clinicians with more efficient workflows, higher confidence in the clinician's abilities, and may reduce patient visits. Also, the micro-level guidance to the clinician could lead to non-observer biased measurements and a new standard in measuring the aggressiveness of tumors, which would impart either patience or urgency in treating a suspect tumor.

Figure 1:
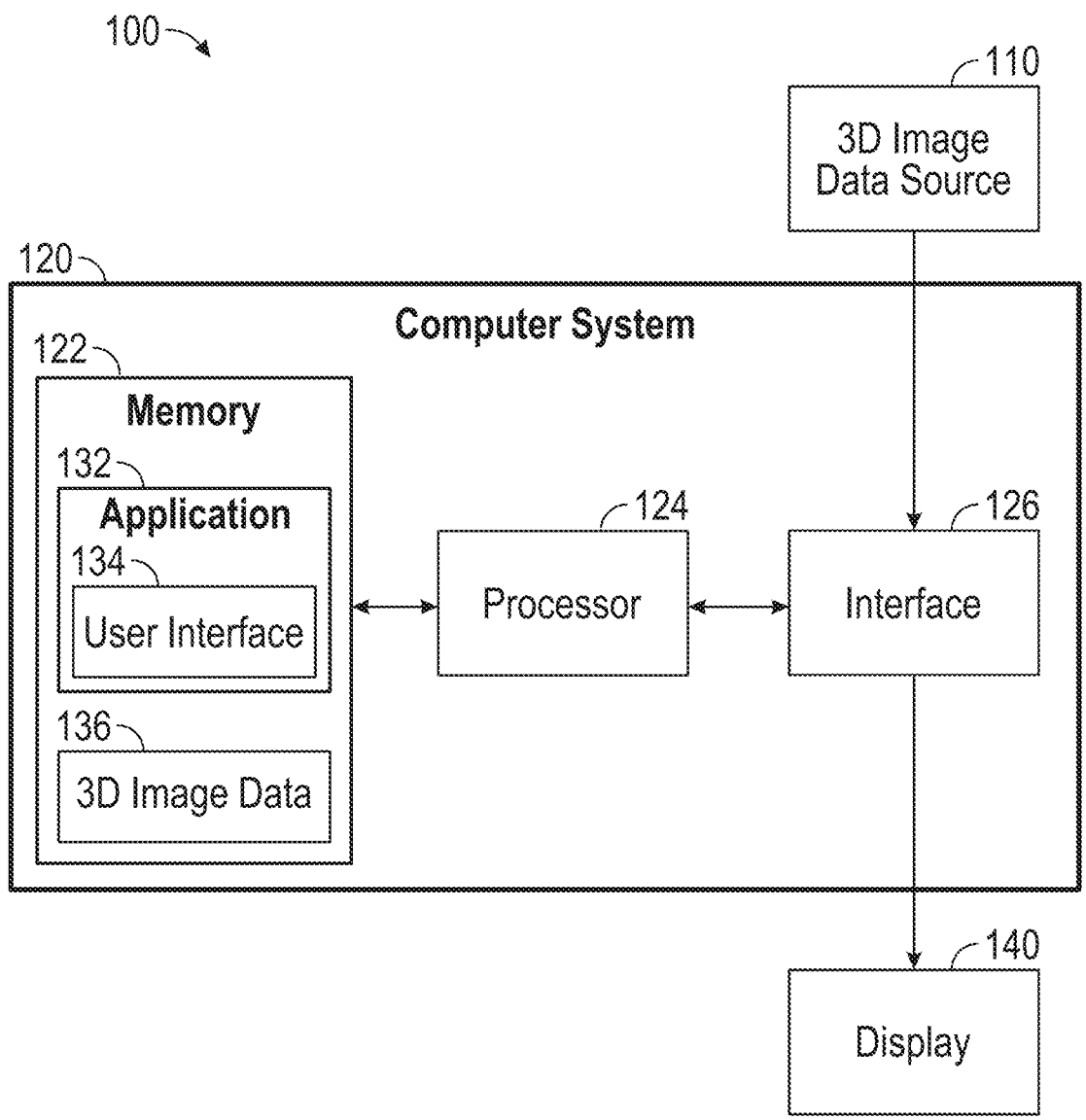
FIG. 1 is a block diagram of a system for detecting a nodule and guiding a surgical procedure in accordance with the disclosure.

Reference is now made to FIG. 1, which is a schematic diagram of a system 100 configured for use with the methods of this disclosure. System 100 may include a computer system 120, which may be coupled to a 3D image data source 110 such as a CT scanner or an MRI, directly or indirectly, e.g., by wireless communication. Computer system 120 may include a memory 122, a processor 124, and an interface 126. Processor 124 may include one or more hardware processors. Memory 122 may store an application 132 and 3D image data 136.

Application 132 may include a user interface 134. Accordingly, the application 132 may, when executed by the processor 124, cause the display 140 to present the user interface 134. The user interface 134 may be configured to present to the user a variety of maps and the 3D image data 136. The user interface 134 may be further configured to display and modify, e.g., mark, aspects of the maps and 3D image data 136 depending on their purpose, function, importance, etc.

3D image data 136 may include 3D image data sets such as CT or MRI image data sets. Processor 124 may be coupled to memory 122. The processor 124 may be coupled to the interface 126, such that the processor 124 may control and/or communicate with the display 140, one or more input devices and/or output devices (not shown), and the 3D image data source 110. The 3D image data source 110 may include a database, a computed tomography (CT) scanner, a magnetic resonance imaging (MRI) system, a C-arm fluoroscope, an ultrasound system, an X-ray system, a positron emission tomography (PET) scanner, and/or any other imaging device suitable for capturing 3D image data 136.

Application 132 may include instructions executable by the processor 124 for executing the methods of this disclosure. For example, as described in detail below, the application 132 may read the 3D image data 136, which was received from the 3D image data source 110, identify volumetric parameters or one or more boundaries of a nodule in the 3D image data, generate a voxel map of the nodule defined by the volumetric parameters or one or more boundaries, determine maximum and minimum attenuation values in the voxel map, calculate a gradient and/or a gradient curve based on the voxel map and the maximum and minimum attenuation values, and generate a volumetric vector map, a gradient map, or a gradient plot based on the result of calculating the gradient and/or the gradient curve. Calculating the gradient and/or gradient curve may include calculating the maximum and minimum gradient values across the voxel map. Application 132 may also generate vector arrows and/or a heat map based on the volumetric vector map, gradient map, or gradient plot, and cause the display 140 to display the vector arrows and/or the heat map. Application 132 may cause the display 140 to display all or a portion of the 3D image data 136 and display the vector arrows and/or the heat map overlaid on the 3D image data 136.

The computer system 120 may be a stationary computing device, such as a personal computer, or a portable computing device such as a tablet computer. The computer system 120 may embed a plurality of computer devices. The input devices may include any devices by which a user may interact with the computer system 120, such as, for example, a mouse, keyboard, foot pedal, touch screen, and/or voice interface, e.g., a microphone. The output devices may include any connectivity port or bus, such as, for example, parallel ports, serial ports, universal serial busses (USB), and/or any other similar connectivity port known to those skilled in the art. In some aspects, the computer system 120 may be part of a diagnostic system, a navigation system, a surgical robotic system, and/or similar type of medical system. Accordingly, the methods of the disclosure may be incorporated into the workflow for diagnostic and/or surgical procedures. For example, the diagnostic system may automatically or semi-automatically identify one or more "hot spots" or concentrations of malignant tissue within a nodule. The navigation system may display the one or more "hot spots" in a volumetric vector map, e.g., a heat map, to help a clinician guide a tool, e.g., a biopsy tool, to the one or more "hot spots." The surgical robotic system may include an arm and an end effector that holds and manipulates a tool, e.g., a biopsy tool. The surgical robotic system may control the arm and/or the end effector to navigate the tool to the one or more "hot spots" of malignant tissue based on the heat map.

Memory 122 may include any non-transitory computer-readable storage media for storing data and/or software including instructions that are executable by processor 124 and which control the operation of computer system 120 and, in some aspects, may also control the operation of the 3D image data source 110. In an aspect, memory 122 may include one or more storage devices such as solid-state storage devices, e.g., flash memory chips. Alternatively, or in addition to the one or more solid-state storage devices, memory 122 may include one or more mass storage devices connected to the processor 124 through a mass storage controller (not shown) and a communications bus (not shown).

In aspects, the interface 126 of FIG. 1 may be configured as a network interface. The network interface may be configured to connect to a network such as a local area network (LAN) consisting of a wired network and/or a wireless network, a wide area network (WAN), a wireless mobile network, a Bluetooth network, and/or the Internet. The network interface may be used to connect between the computer system 120 and an imaging device that is serving as the 3D image data source 110. The network interface may be also used to receive image data from the imaging device.

Figure 2:
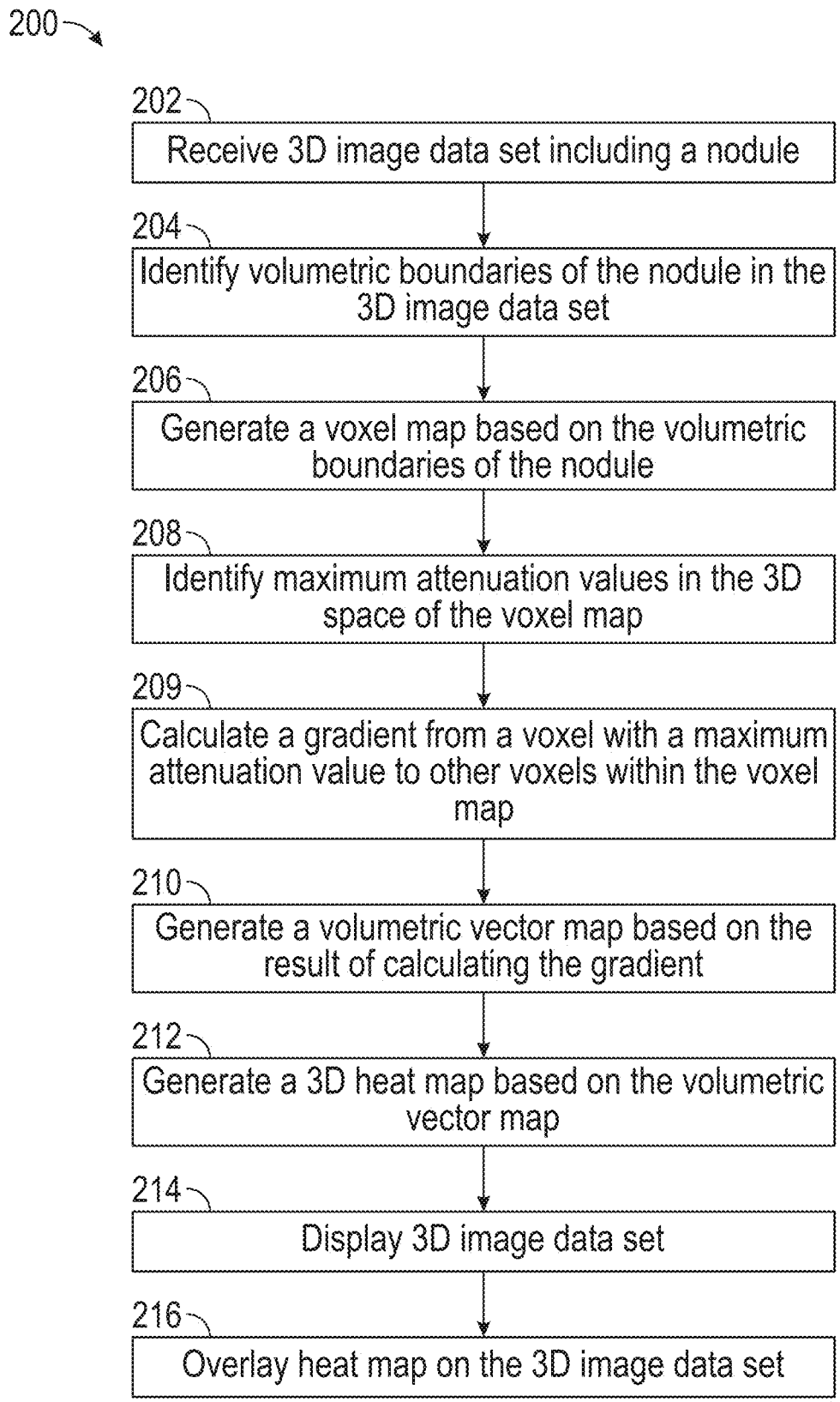
FIG. 2 is a flowchart that illustrates a method of generating and displaying a volumetric vector map based on 3D image data.

FIG. 2 shows an example of a method for generating and displaying a volumetric vector map according to aspects of this disclosure. At block 202, a three-dimensional (3D) image data set including a nodule is received or acquired from a 3D image data source, e.g., the 3D image data source 110 of FIG. 1. At block 204, the 3D image data set is read and volumetric parameters, e.g., boundaries, of the nodule are identified in the 3D image data set. The volumetric boundaries of the nodule may be identified by performing a suitable image processing method on the 3D image data set. The image processing method may identify attenuation value "spikes," which represent the boundary between nodule tissue and normal or healthy tissue. The image processing method may identify attenuation value "spikes" by determining whether voxels are greater than a threshold attenuation value indicating the presence of a nodule. The threshold attenuation value selected for identifying a nodule may depend on a number of factors including the characteristics of the patient's anatomy, the nodule, and the presentation of the nodule. For example, for lung nodules, the attenuation values may range between about 0 Hounsfield units (HU) and about 500 HU. The upper limit of the attenuation values may be greater if the lung nodule is calcified. If cavitation is exhibited, such as in tuberculosis (TB), the lower limit of the attenuation values may extend below 0 HU toward −1000 HU. In some aspects, the attenuation values may range between about −100 HU and about 200 HU.

The image processing method may include a segmentation algorithm or an edge detection algorithm that finds edges of the nodule. The segmentation algorithm may be configured by seeding and/or learning parameters suitable for identifying the volumetric parameters of the nodule. In some aspects, identifying the volumetric boundaries may include presenting a user interface that the clinician can use to mark at least a portion of the volumetric boundaries of the nodule. The marked volumetric boundaries of the nodule may be used to train the image processing method.

At block 206, a voxel map is generated based on the volumetric boundaries of the nodule identified in the 3D image data set. For example, each voxel of the nodule defined by the volumetric boundaries may be assigned an attenuation value. At block 208, the maximum attenuation values (e.g., Hounsfield units) are identified in the 3D space of the voxel map. In some aspects, minimum attenuation values are identified in the 3D space of the voxel map. In cases where there are multiple hot spots in a nodule, block 208 may include identifying multiple local maximum and minimum attenuation values. In some aspects, the method may include calculating an average or mean attenuation value and using the mean attenuation value as a reference attenuation value to identify the maximum and minimum attenuation values. One or more mean attenuation values may be calculated based on attenuation values inside the nodule and/or based on attenuation values outside of the nodule in an adjacent volume. For example, the method may calculate a mean attenuation value inside the nodule and a mean attenuation value outside the nodule. The minimum attenuation value may correspond to an attenuation value of tissue adjacent to the nodule.

Differential calculus may then be applied across the 3D space of the voxel map to develop a volumetric vector map of the partial differential equation from the voxel with the highest Hounsfield unit to the margin or nodule boundary. The margin or nodule boundary may be represented by a series of multiple interconnected contours in three-dimensional space. The boundary may be defined by a function based on a continuously-connected asymptotic response of the attenuation values with respect to the nodule. In other words, low-high-low attenuation values across a small gap of voxels and all voxels that match that response are connected to form a volume. A triple integral may define the function which defines the volume. For example, at block 209, a gradient of the voxel map or a gradient curve is calculated from the voxel with the maximum attenuation value to other voxels within the volumetric boundary. The gradient indicates where one or more peaks are located with respect to the tissue surrounding the nodule. In some aspects, the gradient or gradient curve is calculated from the voxel with the maximum attenuation value to the voxel with the minimum attenuation values, or from voxels with local maximum attenuation values to voxels with local minimum attenuation values, respectively.

The gradient may be calculated according to the following calculations. For a real-valued function $f(x, y, z)$ on $R^3$, which may be the voxel map, the gradient $\nabla f(x, y, z)$ is a vector-valued function on $R^3$ where the gradient's value at a point $(x, y, z)$ is the vector:

$$\nabla f(x,y,z)=(\partial f/\partial x,\partial f/\partial y,\partial f/\partial z)=(\partial f/\partial x)i+(\partial f/\partial y)j+(\partial f/\partial z)k$$

in $R^3$, where each of the partial derivatives is evaluated at the point (x, y, z).

At block 210, a volumetric vector map is generated based on the result of calculating the gradient. The volumetric vector map may be displayed to a clinician in a 3D volumetric form with vector arrows (as in a phase portrait) and/or a heat map. For example, at block 212, a 3D heat map is generated based on the volumetric vector map. The 3D heat map may be generated by associating a range of colors with a range of the gradient vectors in the volumetric vector map and generating a 3D representation of the nodule such that points of the 3D representation of the nodule corresponding to the gradient vectors are colored according to the magnitude of the gradient vectors.

Figure 4:
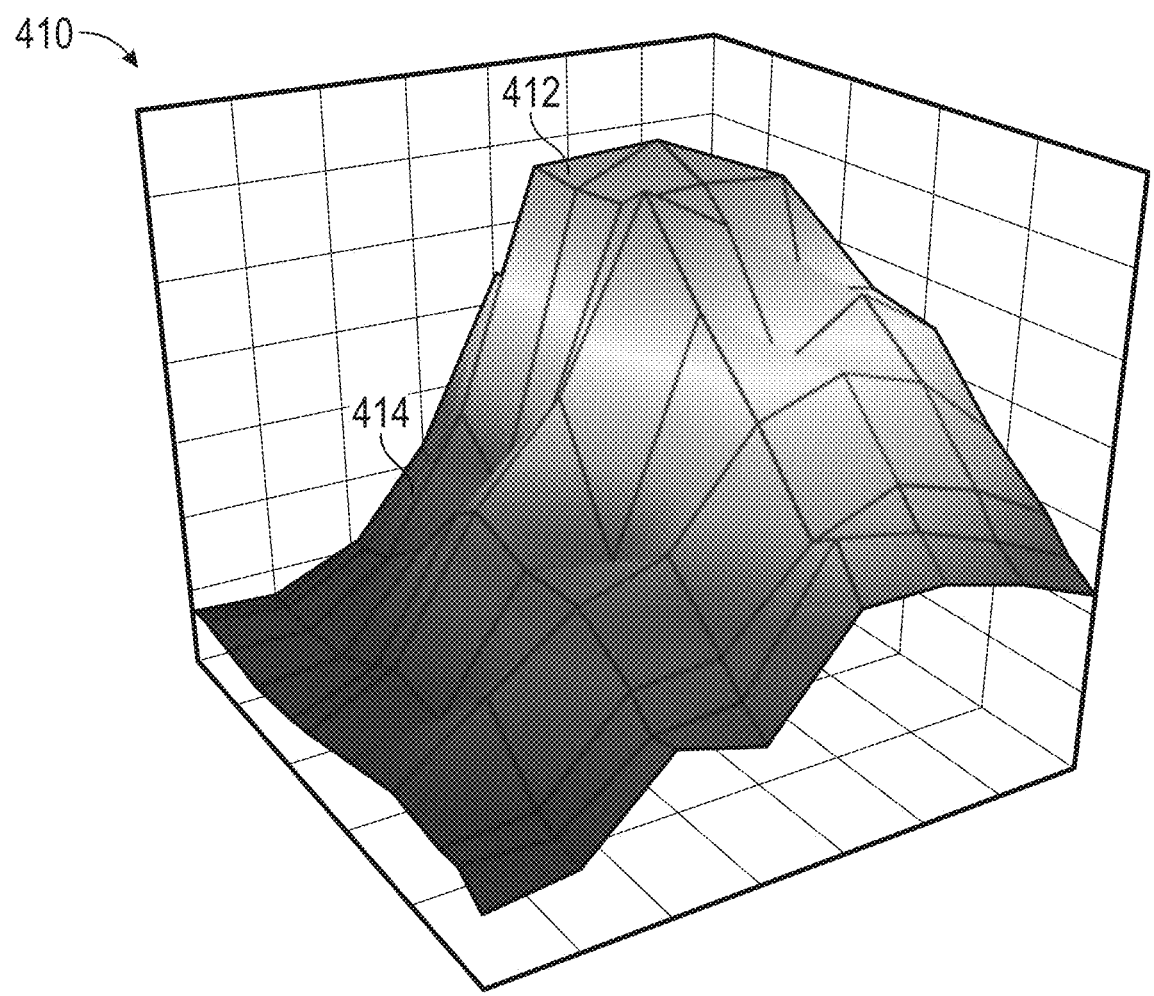
FIGS. 4 and 5 are schematic diagrams that illustrate heat maps, which are based on a volumetric vector map, and which are displayed to the clinician to help the clinician treat a nodule.

For example, FIG. 4 illustrates a portion of a 3D heat map in which a continuous range of colors are used to illustrate the range of gradient values (e.g., from strongest gradients to weakest gradients or from a voxel having a maximum gradient to the margin), which represent the range of nodule characterizations from benign to malignant. The shades of the color orange 412 may represent large gradients in the attenuation values or the most malignant tissue while the shades of the color blue 414 may represent small gradients in the attenuation values or the most benign tissue.

In one aspect, a user interface may be presented to the clinician that enables the clinician to change the view of or otherwise manipulate the 3D heat map to help the clinician better visualize the nodule in preparation for a medical procedure. For example, the user interface may enable the clinician to take axial, coronal, and/or sagittal cross sections of the 3D heat map. The ability to view cross sections of the 3D heat map may enable the clinician to find an area within the 3D heat map. The user interface may also enable a clinician to rotate the 3D heat map. The clinician may use the user interface to review the 3D heat map in order to determine a location or area within the lesion to biopsy.

Figure 5:
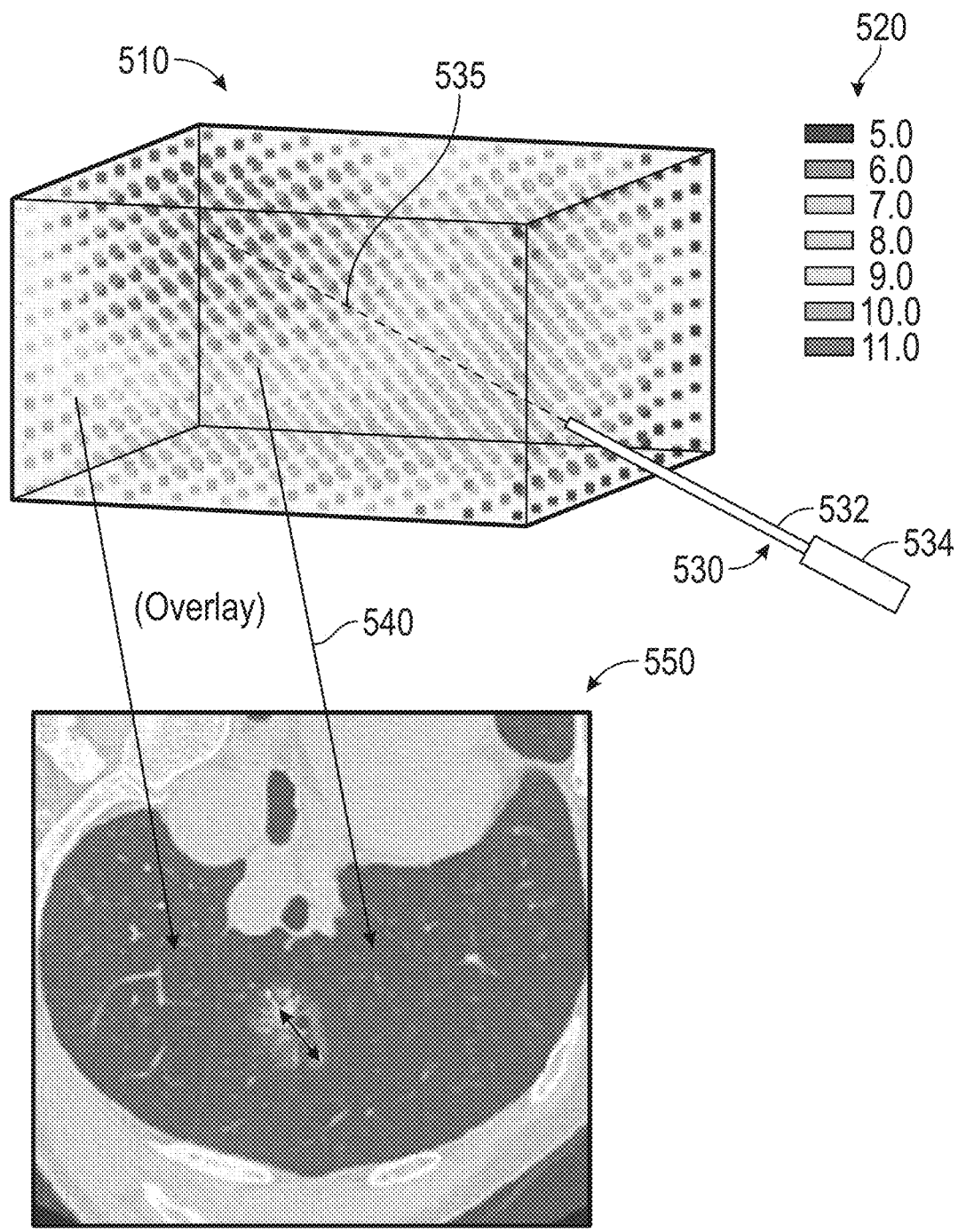

FIG. 5 illustrates another example of displaying a volumetric vector map in the form of a surface mesh. As shown in the legend 520, seven colors represent different ranges of gradient values. Then, spaced points in the volumetric vector map are colored according to the gradient value calculated at each of the spaced points. Alternatively, vector arrows may be generated and displayed at each of the points. The length and direction of the vector arrows at each of the points may be determined based on the magnitude and direction of the gradient calculated at each of the points. In one aspect, a user interface may present a view or window showing a contour plot. In the view, the contour plot may be projected onto a two-dimensional slice of the 3D image data set.

At block 214, the 3D image data set is displayed. In aspects, all or a portion of the 3D image data set may be displayed. For example, as illustrated in FIG. 5, a relevant slice 550 of a CT image data set is displayed. Then, at block 216, the heat map is overlaid on the 3D image data set. For example, the 3D heat map 510 is overlaid 540 or projected on the relevant slice 550 of the CT image data set. Alternatively, the relevant slice 550 or multiple slices may be aligned with the 3D heat map 510 such that the relevant slice 550 intersects with the 3D heat map 510.

After overlaying the heat map on the CT image data set, the heat map overlaid on the CT image data may be displayed to a clinician on a display screen and may be referenced perioperatively to guide the clinician on where to place an ablation tool (e.g., in the case of thermal ablation), where to deposit pharmaceuticals (e.g., injection of chemotherapy medicines, immunotherapies, or targeted viruses), where to concentrate the biopsy samples, or where to cut the tissue when resection is indicated.

In aspects, the application 132 may include a path planning application, which processes the volumetric vector map to determine a path to a desired location within the nodule and displays the path 535 on the 3D heat map 510 of FIG. 5. In the case of a lung treatment procedure, the path planning application may determine an optimal entry point to a lung nodule based on the volumetric vector map and determine an optimal path for a bronchoscopic tool through a luminal network of the lungs to reach the optimal entry point. The optimal entry point may be an entry point that is optimal for taking a biopsy of the most malignant tissue of the lung nodule. The path planning application may also determine and display a length and angle of the biopsy needle resulting in the greatest probability of highest yield.

In aspects where an ablation tool 530 is employed, the ablation tool 530, including an antenna 532 and a handle 534, may be displayed on the display 140 of the system 100 of FIG. 1. In other aspects, any other tool suitable for treating a nodule, e.g., an endoscopic tool or a biopsy tool, may be displayed on the display 140 to help the clinician guide the tool to one or more entry points to the nodule and/or through the nodule to one or more areas within the nodule. The one or more areas within the nodule may correspond to one or more hot spots in a heat map that indicate the most malignant tissue portions within the nodule. The tool may be a needle, such as a biopsy needle, used for intra-tumoral injection of immunotherapy or chemotherapy.

Additionally, or alternatively, other views may be displayed to the clinician. For example, a gun barrel view may be displayed showing the view from the tip of a catheter, a biopsy needle, or an endoscope with respect to the nodule or an area or location within the volumetric vector map. The user interface may display a value of the distance between the tip and the area or location within the volumetric vector map.

Those of skill in the art will understand that while generally described in conjunction with CT image data, that is a series of slice images that make up a 3D volume, the disclosure is not so limited and may be implemented in a variety of imaging techniques including magnetic resonance imaging (MRI), fluoroscopy, X-Ray, ultrasound, positron emission tomography (PET), and other imaging techniques that generate 3D image volumes without departing from the scope of the disclosure. Further, those of skill in the art will recognize that a variety of different algorithms may be employed to segment the CT image data set including connected component, region growing, thresholding, clustering, watershed segmentation, edge detection, and others.

Those of ordinary skill in the art will recognize that the methods and systems described herein may be embodied on one or more applications operable on a computer system for a variety of diagnostic and therapeutic purposes. As an initial matter, these systems and methods may be embodied on one or more educational or teaching applications. Further the methods and systems may be incorporated into a procedure planning system where anatomical structures, nodules, and other features found in the 3D image data are identified and a surgical or interventional path is planned to enable biopsy or therapy to be delivered at a desired location. Those of skill in the art will recognize that a variety of additional and complementary uses of the image processing and display methods described herein.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Although the description of computer-readable media contained herein refers to solid-state storage, it should be appreciated by those skilled in the art that computer-readable storage media can be any available media that can be accessed by the processor. That is, computer readable storage media may include non-transitory, volatile and non-volatile, removable and non-removable media implemented in any method or technology for storage of information such as computer-readable instructions, data structures, program modules or other data. For example, computer-readable storage media may include RAM, ROM, EPROM, EEPROM, flash memory or other solid-state memory technology, CD-ROM, DVD, Blu-Ray or other optical storage, magnetic cassettes, magnetic tape, magnetic disk storage or other magnetic storage devices, or any other medium which may be used to store the desired information, and which may be accessed by the computer system 120.

While several aspects of the disclosure have been shown in the drawings, it is not intended that the disclosure be limited thereto, as it is intended that the disclosure be as broad in scope as the art will allow and that the specification be read likewise. For example, the systems and methods of the disclosure can be applied to tumors in the liver, the colon, the rectum, the prostate, the pancreas, the kidney, the neck, and the brain. Therefore, the above description should not be construed as limiting, but merely as examples of particular aspects.

What is claimed is:

1. A system comprising:
 a processor;
 a display coupled to the processor;
 a memory coupled to the processor and having stored thereon instructions, which when executed by the processor, causes the processor to:
  receive a three-dimensional (3D) image data set of a nodule;
  identify volumetric parameters of the nodule in the 3D image data set;
  generate a voxel map based on the volumetric parameters of the nodule;
  determine maximum and minimum attenuation values in the voxel map;
  calculate a gradient based on the voxel map and the maximum and minimum attenuation values;
  generate a volumetric vector map based on a result of calculating the gradient; and
  cause the display to display the volumetric vector map.

2. The system of claim 1, wherein the instructions, when executed by the processor, further cause the processor to:
 generate vector arrows based on the volumetric vector map; and
 cause display of the vector arrows on the display.

3. The system of claim 1, wherein the instructions, when executed by the processor, further cause the processor to:
 generate a heat map based the volumetric vector map; and
 cause display of the heat map on the display.

4. The system of claim 1, wherein the instructions, when executed by the processor, further cause the processor to:
 overlay the volumetric vector map on the 3D image data set; and
 cause display of the volumetric vector map overlaid on the 3D image data set on the display.

5. The system of claim 1, wherein the 3D image data set is a computed tomography (CT) image data set, a magnetic resonance imaging (MRI) data set, a fluoroscopic image data set, an X-Ray image data, an ultrasound image data set, or a positron emission tomography (PET) image data set.

6. The system of claim 1, wherein the instructions, when executed by the processor, further cause the processor to apply a differential equation across a 3D space of the voxel map to generate the volumetric vector map.

7. A method comprising:
 acquiring three-dimensional (3D) image data of a nodule;
 identifying volumetric boundaries of the nodule in the 3D image data;
 generating a voxel map based on the volumetric boundaries of the nodule;
 identifying a maximum Hounsfield unit in the 3D space of the voxel map; and
 applying a differential equation across the 3D space of the voxel map from a voxel with the maximum Hounsfield unit to a margin boundary; and
 generating a volumetric vector map based on a result of applying the differential equation across the 3D space of the voxel map.

8. The method of claim 7, wherein the nodule is a tumor of a lung, a liver, a kidney, a pancreas, or a brain.

9. The method of claim 7, wherein applying a differential equation across a 3D space of the voxel map includes applying a gradient function.

10. The method of claim 7, wherein the 3D image data is computed tomography (CT) data, a magnetic resonance imaging (MRI) data, fluoroscopic image data, X-Ray image data, ultrasound image data, or positron emission tomography (PET) image data.

11. The method of claim 7, further comprising:
 generating a 3D matrix of vector arrows based on the volumetric vector map; and
 displaying the 3D matrix of vector arrows.

12. The method of claim 7, further comprising:
 generating a heat map based on the volumetric vector map; and
 displaying the heat map.

13. The method of claim 7, further comprising:
displaying the 3D image data set; and
overlaying the volumetric vector map on the 3D image data set.

14. The method of claim 7, further comprising identifying the volumetric boundaries of the nodule using a deep convolutional neural network.

15. A system comprising:
a processor; and
a memory coupled to the processor and having stored thereon instructions, which when executed by the processor, causes the processor to:
receive three-dimensional (3D) image data of a nodule;
identify a boundary of the nodule in the 3D image data;
generate a voxel map based on the boundaries of the nodule;
determine a maximum Hounsfield unit in a 3D space of the voxel map;
calculate a gradient from a voxel with the maximum Hounsfield unit to other voxels within the voxel map;
generate a volumetric vector map based on a result of calculating the gradient; and
cause display of the volumetric vector map.

16. The system of claim 15, wherein the 3D image data is computed tomography (CT) image data, a magnetic resonance imaging (MRI) data, fluoroscopic image data, X-Ray image data, ultrasound image data, or positron emission tomography (PET) image data.

17. The system of claim 15, wherein the instructions, when executed by the processor, further cause the processor to:
display the 3D image data; and
overlay the volumetric vector map on the 3D image data.

18. The system of claim 17, wherein the instructions, when executed by the processor, further cause the processor to display a guide for a medical procedure in a user interface based on the volumetric vector map.

19. The system of claim 18, wherein the medical procedure includes placing an ablation tool, depositing pharmaceuticals, placing a biopsy tool, or cutting tissue.

20. The system of claim 17, wherein the instructions, when executed by the processor, further cause the processor to:
generate a heat map based on the volumetric vector map; and
display the heat map.

* * * * *